United States Patent
Lightburn et al.

(10) Patent No.: US 11,571,450 B2
(45) Date of Patent: Feb. 7, 2023

(54) AQUEOUS EXTRACTION OF PSYCHOACTIVE COMPOUNDS FROM PSILOCYBIN FUNGUS

(71) Applicant: PSILO SCIENTIFIC LTD, Vancouver (CA)

(72) Inventors: Benjamin Lightburn, Vancouver (CA); Ryan Moss, Vancouver (CA); Lisa Ranken, Vancouver (CA)

(73) Assignee: PSILO SCIENTIFIC LTD, Vancouver (CA)

( * ) Notice: Subject to any disclaimer, the term of this patent is extended or adjusted under 35 U.S.C. 154(b) by 0 days.

(21) Appl. No.: 17/697,798

(22) Filed: Mar. 17, 2022

(65) Prior Publication Data

US 2022/0202886 A1 Jun. 30, 2022

Related U.S. Application Data

(63) Continuation of application No. 17/348,697, filed on Jun. 15, 2021, now Pat. No. 11,331,357, which is a continuation of application No. PCT/CA2021/050813, filed on Jun. 14, 2021.

(60) Provisional application No. 63/040,317, filed on Jun. 17, 2020, provisional application No. 63/046,089, filed on Jun. 30, 2020.

(30) Foreign Application Priority Data

| | | |
|---|---|---|
| Jul. 29, 2020 | (CA) | CA 3088384 |
| Jul. 29, 2020 | (CA) | CA 3124367 |
| Aug. 7, 2020 | (CA) | CA 3089455 |
| Oct. 23, 2020 | (CA) | CA 3097246 |
| Dec. 4, 2020 | (CA) | CA 3101765 |
| Dec. 18, 2020 | (CA) | CA 3103707 |

(51) Int. Cl.

| | |
|---|---|
| *A61K 36/00* | (2006.01) |
| *A61K 36/07* | (2006.01) |
| *A61K 31/4045* | (2006.01) |
| *A61K 31/675* | (2006.01) |
| *A61K 31/48* | (2006.01) |
| *A61K 31/404* | (2006.01) |
| *A61K 31/42* | (2006.01) |

(52) U.S. Cl.
CPC ............ *A61K 36/07* (2013.01); *A61K 31/404* (2013.01); *A61K 31/4045* (2013.01); *A61K 31/42* (2013.01); *A61K 31/48* (2013.01); *A61K 31/675* (2013.01); *A61K 2236/331* (2013.01); *A61K 2236/333* (2013.01); *A61K 2236/39* (2013.01); *A61K 2236/51* (2013.01)

(58) Field of Classification Search
CPC .............................................. A61K 2236/331
See application file for complete search history.

(56) References Cited

U.S. PATENT DOCUMENTS

| | | |
|---|---|---|
| 3,183,172 A | 5/1965 | Roger et al. |
| 8,846,075 B2 | 9/2014 | Jonsson et al. |
| 9,308,175 B2 | 4/2016 | Pellikaan et al. |
| 2017/0157343 A1 | 6/2017 | Davidson et al. |
| 2019/0142851 A1 | 5/2019 | Chadeayne |
| 2020/0375967 A1 | 12/2020 | Stamets |

FOREIGN PATENT DOCUMENTS

| | | |
|---|---|---|
| CA | 2339353 A1 | 4/2000 |
| CA | 2794734 A1 | 10/2011 |
| CA | 3050679 A1 | 7/2018 |
| CA | 3052974 A1 | 8/2018 |
| CA | 3078765 A1 | 4/2019 |
| CA | 3088384 A1 | 10/2020 |
| CA | 3137106 A1 | 10/2020 |
| CA | 3097246 A1 | 11/2021 |
| CN | 101292727 A | 10/2008 |
| DE | DD 264023 A1 * | 1/1989 |
| GB | 911946 A | 12/1962 |
| WO | WO-03074526 A2 | 9/2003 |
| WO | WO-2019073379 A1 | 4/2019 |
| WO | WO-2021003467 A1 | 1/2021 |

(Continued)

OTHER PUBLICATIONS

Anastos N. et al., "The Determination of Psilocin and Psilocybin in Hallucinogenic Mushrooms by HPLC Utilizing a Dual Reagent Acidic Potassium Permanganate and Tris(2,20-bipyridyl)ruthenium(II) Chemiluminescence Detection System", J Forensic Sci 51(1): 45-51 (2006).

Casale JF. An aqueous-organic extraction method for the isolation and identification of psilocin from hallucinogenic mushrooms. J Forensic Sci. Jan. 1985;30(1):247-50.

De Boer P, "Simple method of psilocybin extraction", Blog: Fresh Truffles and Growkits Jun. 24, 2017 (Jun. 24, 2017).

Gartz, Extraction and analysis of indole derivatives from fungal biomass. Journal of Basic Microbiology 34(1): 17-22 (1994).

Kunle et al, Standardization of herbal medicines—a review, Int. J. Biodivers. Conserv. 4(3): 101-112 (2012).

Kysilka and Wurst, "A novel extraction procedure for psilocybin and psilocin determination in mushroom samples", Planta Medica 56(3): 327-328 (1990).

(Continued)

*Primary Examiner* — Qiuwen Mi
(74) *Attorney, Agent, or Firm* — Wilson Sonsini Goodrich & Rosati

(57) ABSTRACT

This invention relates to the extraction of psychoactive compounds from psilocybin fungus for use in medicine. Raw psilocybin fungus is dried and ground. The solvent used for extraction is a lower aliphatic alcohol, water, a hydro-alcohol mixture, an acidic hydro-alcohol mixture, or an alkaline hydro-alcohol mixture. The extraction slurry is filtered and pH-adjusted if necessary. The solvent is then partially evaporated, or completely evaporated with water added back, to form a concentrated slurry. The concentrated slurry is then standardized to provide a known concentration of the psychoactive alkaloids that have been extracted. The standardized slurry may then be dried to result in a powdered psilocybin mushroom extract with a precisely defined purity.

21 Claims, 8 Drawing Sheets

(56) References Cited

FOREIGN PATENT DOCUMENTS

WO    WO-2021007152 A1    1/2021

OTHER PUBLICATIONS

Mikey's Psilly Ethanol Extract (2017).
Moldavan et al., The effect of Psilocybe cubensis extract on hippocampal neurons in vitro, Fiziol Zh. 47(6): 15-23 (2001).
Nguyen et al., Optimization of Spray Drying Condition from Trametes Versicolor Mushroom Extract. Journal of Science and Technology 39A: 25-30 (2019).
PCT/CA2021/050813 International Search Report dated Sep. 9, 2021.
PCT/CA2021/050822 International Search Report dated Oct. 19, 2021.
PCT/CA2021/050823 International Search Report dated Sep. 20, 2021.
PCT/CA2021/051891 International Search Report and Written Opinion dated Feb. 28, 2022.
Perkal, M., et al. "Determination of hallucinogenic components of Psilocybe mushrooms using high-performance liquid chromatography." J. Chromatography A 196 (1980), pp. 180-184.
Poliwoda et al., Determination of muscimol and ibotenic acid in mushrooms of Amanitaceae by capillary electrophoresis. Electrophoresis 35(18):2593-2599 (2014).
Psilocybin Expert, "Formulating New "Magic Mushroom" compositions", Psilocybin Technology, Feb. 13, 2018 (Feb. 13, 2018).
Roderick, "Psilocybin and Cannabis Cocktails", Psillow website, Dec. 29, 2019 (Dec. 29, 2019).
Truffle Magic—Simple Method of Psilocybin Extraction (2017).
Uneasy1, "Psilocin HCI extraction" Chemistry mdma hiveboard (2003). Https://chemistry.mdma.ch/hiveboard/tryptamine/000448065.html.
U.S. Appl. No. 17/348,697 Non-Final Office Action dated Dec. 13, 2021.
U.S. Appl. No. 17/348,697 Notice of Allowance dated Feb. 7, 2022.
U.S. Appl. No. 17/348,697 Notice of Allowance dated Mar. 22 2022.
U.S. Appl. No. 17/351,149 Final Office Action dated Jan. 24, 2022.
U.S. Appl. No. 17/351,149 Non-Final Office Action dated Oct. 13, 2021.
U.S. Appl. No. 17/351,149 Notice of Allowance dated Apr. 29, 2022.
U.S. Appl. No. 17/351,149 Notice of Allowance dated Mar. 21, 2022.
U.S. Appl. No. 17/483,601 Non-Final Office Action dated Dec. 13, 2021.
U.S. Appl. No. 17/483,601 Notice of Allowance dated Feb. 25, 2022.
U.S. Appl. No. 17/483,601 Notice of Allowance dated Feb. 4, 2022.
U.S. Appl. No. 17/587,731 Non-Final Office Action dated Jul. 12, 2022.
Mahmoudi E, et al. Alteration of depressive-like behaviors by psilocybe cubensis alkaloid extract in mice: The role of glutamate pathway. Research Journal of Pharmacognosy 5(2): 17-24 (2018).
Ojha A, et al. Recent advancement in emulgel: A novel approach for topical drug delivery. Int. J. Adv. Pharm, 6(01), 17-23 (2017).
Passie T, et al. The pharmacology of psilocybin. Addiction biology, 7(4), pp. 357-364 (2002).
PCT/CA2021/051495 International Search Report and Written Opinion dated Jan. 26, 2022.
PCT/CA2021/051701 International Search Report and Written Opinion dated Feb. 1, 2022.
PCT/CA2021/051702 International Search Report and Written Opinion dated Mar. 2, 2022.
PCT/CA2021/051876 International Search Report and Written Opinion dated Mar. 29, 2022.

* cited by examiner

AQUEOUS EXTRACTION OF PSYCHOACTIVE COMPOUNDS FROM PSILOCYBIN FUNGUS

RELATED APPLICATIONS

This application is a continuation of U.S. patent application Ser. No. 17/348,697 filed Jun. 15, 2021, which is a continuation of International Application No. PCT/CA2021/050813 filed Jun. 14, 2021, which claims priority from Canadian Application No. 3089455 filed on Aug. 7, 2020, and Canadian Application No. 3088384 filed on Jul. 29, 2020, which claim the benefit of U.S. Provisional Patent Application No. 63/040,317 filed on Jun. 17, 2020, and U.S. Provisional Patent Application No. 63/046,089 filed on Jun. 30, 2020, each of which are incorporated by reference in their entireties, International Application No. PCT/CA2021/050813 also claims priority to Canadian Application No. 3097246 filed on Oct. 23, 2020, Canadian Application No. 3101765 filed on Dec. 4, 2020, and Canadian Application No. 3103707 filed on Dec. 18, 2020, this application also claims priority to Canadian Application No. 3124367 filed on Jul. 29, 2020, each of which are incorporated by reference in their entireties.

TECHNICAL FIELD

This application relates to the extraction of active ingredients from fungus. More specifically, it relates to extracting psychoactive compounds from psilocybin fungus and forming an extract of known purity.

BACKGROUND

Varieties of mushrooms have played important roles in most societies. The active ingredients in mushrooms, especially psilocybin mushrooms with psychoactive compounds such as psilocybin, psilocin, baeocystin, norbaeocystin, and norpsilocin, have been found to have medicinal properties including relief of symptoms of various diseases and conditions. The concentration of active psilocybin mushroom compounds varies not only from species to species, but also from mushroom to mushroom inside a given species, subspecies or variety. The same holds true even for different parts of the same mushroom or mycelium.

Various methods of extraction, which have been used to separate natural extracts from a variety of mushrooms, have resulted in difficulties with large crop-to-crop variability. This is as well as the problem of a large variability within a single plant or fungus in terms of the concentration of the active psychoactive compound and its stability. Different solvent choices extract the psychoactive compounds equally, some of them electively extract one or the other, and some convert the compounds between each other or degrade them into non-psychoactive compounds. Many extraction processes for extracting standardized concentrations of the compounds for direct medical use are usually complex. This results in expensive extraction processes and a high cost of isolated, natural extracts.

U.S. Pat. No. 3,183,172 to Heim et al. relates to an industrial process for the isolation of active compounds from mushrooms grown under predetermined conditions. With the predetermined growing conditions, mushrooms grow with ten times more active mycelium and sclerotium, and increased concentrations of psychoactive compounds. However, a large portion of the target compounds are lost during the extraction process or not extracted at all. In addition, the solvent and solvent systems used during the extraction process are materials such as methanol, acetone, dichloromethane, diethyl ether or others known to be toxic to humans, even in small quantities. These problems are significant with respect to very potent extracts of psilocybin mushrooms, considering that a normal dose for use ranges from only 5 mg to 25 mg. The extracted psychoactive compounds are generally without a stable and standardized concentration.

To date, the focus has largely been on synthetic preparations of these compounds because of the many difficulties associated with naturally extracted preparations. It is currently infeasible and expensive to extract psilocybin from mushrooms, and even the best chemical synthesis methods require expensive and difficult-to-source starting substrates.

Accordingly, there is a need of methods to produce high efficiency, standardized preparations of the target compounds for medical use while using acceptable solvent systems to create a more consistent supply chain.

This background information is provided to reveal information believed by the applicant to be of possible relevance to the present invention. No admission is necessarily intended, nor should be construed, that any of the preceding information constitutes prior art against the present invention.

SUMMARY OF INVENTION

The present invention is directed to an extraction process of psychoactive compounds from psilocybin fungus, for example, the *Psilocybe cubensis* species of psychedelic mushroom. The principal psychoactive compounds in *Psilocybe cubensis* include psilocybin and psilocin. In particular, the extraction process of psychoactive compounds involves drying fresh *Psilocybe cubensis*, followed by grinding, extraction with a solvent in one or more steps, one or more steps of filtration, optional adjustment of the pH if the solvent is acidic (acid/water/alcohol) or alkaline (base/water/alcohol), evaporation of the solvent, and standardization. Optionally, the process includes drying to result in a final powdered psilocybin mushroom extract.

This summary does not necessarily describe all features of the invention.

Disclosed herein is a process for forming an extract of psychoactive alkaloids from psilocybin fungus comprising the steps of: soaking a biomass of dried, raw psilocybin fungus in a solvent selected from the group consisting of ethanol, a water-ethanol mixture, and water in order to dissolve the psychoactive alkaloids in the solvent; filtering an undissolved portion of the biomass from the solvent; evaporating a portion of the solvent to form a concentrated slurry; and standardizing the concentrated slurry by adding thereto a quantity of carrier measured to achieve a specified purity of extract. In some embodiments, the standardizing comprises measuring a psychoactive alkaloid content in the concentrated slurry, and using the psychoactive alkaloid content, the specified purity and a volume of the concentrated slurry to determine the quantity of carrier.

BRIEF DESCRIPTION OF DRAWINGS

The following drawings illustrate embodiments of the invention, which should not be construed as restricting the scope of the invention in any way.

DESCRIPTION

A. Glossary

Psilocybin fungi, or psilocybin mushrooms—these are from a group of fungi that contain at least one psychoactive alkaloid, and generally contain psilocybin and psilocin. They may also contain other psychoactive alkaloids such as baeocystin, norbaeocystin and norpsilocin. The genera of these mushrooms include *Copelandia, Gymnopilus, Inocybe, Panaeolus, Pholiotina, Pluteus*, and *Psilocybe.*

*Psilocybe* mushrooms—these form a genus of gilled mushrooms in the family Hymenogastraceae. Most species contain the psychedelic alkaloids psilocybin, psilocin and baeocystin.

Psilocybin—this is a psychedelic prodrug produced by numerous species of mushrooms, collectively known as psilocybin mushrooms. Psilocybin is converted by the body to psilocin, which has mind-altering effects such as euphoria and hallucinations, but can also lead to nausea and panic attacks.

B. Process Overview

Figure 1:
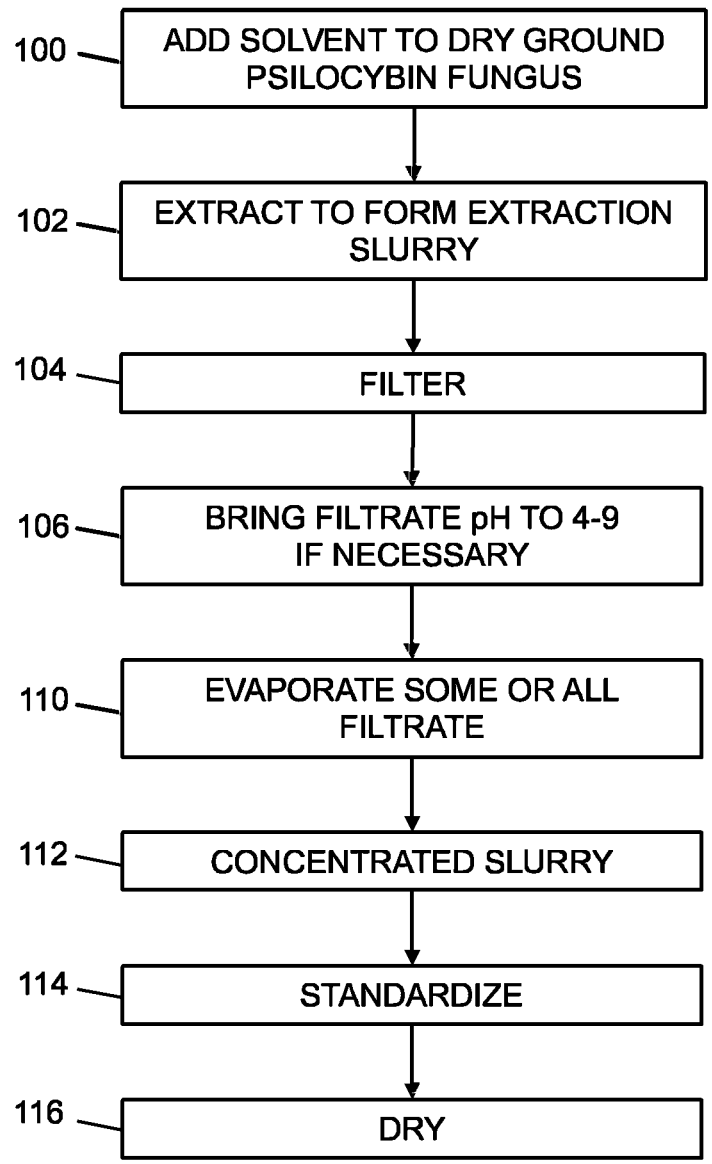
FIG. 1 is a high-level flowchart showing the key steps of a process for extracting psychoactive alkaloids from psilocybin fungus, according to an embodiment of the present invention.

Referring to FIG. 1, a flowchart is shown of the basic steps of the extraction process for extracting psychoactive compounds from psilocybin fungus. In step 100, a solvent is added to a biomass of dried and ground, raw psilocybin fungus. The raw psilocybin fungus includes *Psilocybe cubensis* mushrooms, *Psilocybe cyanescens* mushrooms, or a mixture of these. Other species of psilocybin mushrooms may also be used.

The parts of the mushrooms used include, for example, caps, gills, stems, and hyphae, and more particularly, any part of the psilocybin mushroom or mycelium can be included. In other cases, the raw psilocybin fungus parts used include only caps, or only stems, or only gills, or only hyphae or only mycelium or any mixture thereof. In still other cases, parts of the raw psilocybin fungus used are those that would normally be considered waste, in which valuable psychoactive compounds are found only in lower concentrations. The mushroom parts may be ground using a milling machine or pulverization device, for example.

Ideally, the moisture content of the raw plant material after drying is low compared to the total dried biomass weight. For example, the moisture content may be under 5% for smaller scale extractions and under 10% for larger scale extractions. Wet mushrooms, e.g. with a moisture above 80%, will degrade rapidly. Dried biomass lends itself well to extraction since the drying process usually breaks down cell walls, allowing solvent to capture the molecules inside. The temperature of the oven and the drying time depend on how much moisture is in the raw psilocybin fungus, and on the quantity of raw psilocybin fungus.

The solvent may be selected from a range of different solvents, including lower aliphatic alcohols (C=1, 2, 3 or 4), water, alcohol-water mixtures, strong alkaline buffers, and strong acidic buffers. A wide range of solvent to solid ratios can be used. Typically, a 1 to 50:1 solvent-solid ratio (L:kg) may be used for the extraction. The amount of solvent used generally varies according to the weight of the raw psilocybin fungus.

In step 102, as a result of adding the solvent, and soaking the biomass of dried, raw psilocybin fungus in the solvent, essential elements or psychoactive alkaloids found in the biomass dissolve into the solvent. The solvent may be at a low or high temperature, and pressure may be applied to the solvent. In some embodiments the solvent is at room temperature. The optimal temperature of extraction varies depending on the solvent type used for the process. However, the optimal temperature for extraction is in range of 5–95° C. The useful temperature range spans most of the liquid state of the solvent used, and upper and lower limits are determined by physical practicalities and limits of the available apparatus. Still, the temperature of the solvent may be outside of this range in other embodiments. The duration of the extraction is from 10 minutes to 12 hours, with or without agitation. Optimum duration is determined by experimentation, and depends on the chosen solvent and the strength of agitation in the extraction vessel.

If pressure is applied it may be in the range of 50 kPa-100 MPa above atmospheric (7-15000 psig). The lower limit of pressure is indicative of when a benefit is seen in the rate at which the psychoactive alkaloids dissolve in the solvent, since the increased pressure may increase the reaction kinetics of the dissolution of the psychoactive alkaloids into the solvent. The upper limit is determined by what is physically practical given the constraints of equipment to safely operate under high pressure. Nevertheless, other pressures may be used. Solvent composition, particle size and the temperature of extraction will determine how much pressure needs to be applied.

The extraction results in an extraction slurry, which is formed of undissolved and insoluble solids from the mixture of biomass and solvent, which now carries dissolved extract. Some of the undissolved solids may be undesirable components.

In step 104, the extraction slurry is filtered, resulting in a residue (i.e. the undissolved portion of the biomass) and filtrate. The filtering step may be carried out with the extraction slurry still hot, or it may first be allowed to cool. The extraction and filtration steps may be repeated multiple times on the same residue, with a fresh batch of solvent, which may have the same composition as the first solvent or it may be a different solvent.

In step 106, if the filtrate results from using a strongly acidic or alkaline solvent, then the filtrate is brought closer to neutral, e.g. to a pH between 4 and 9 or thereabouts. Desirable effects, such as more complete extraction, or preservation of the alkaloids from decomposition, or the ability to selectively extract certain specific alkaloids, are seen during the extraction stage when stronger acids or alkalis are used compared to weaker ones.

In step 110, evaporation of some or all of the solvent from the filtrate results in a concentrated slurry 112 (liquid and solids) or just solids. If the solvent is methanol, then all of it is evaporated to reduce the likelihood of toxicity. For other solvents, only some of the solvent needs to be evaporated. In the case where solids are obtained from the evaporation, water is added to the solids to form the concentrated slurry 112. The solids tend not to dissolve back into solution because they are less soluble in methanol and ethanol, for example, than water. Also, the solids may be less soluble in the colder water that is added back than the warmer or hotter water that is used for the extraction. Another reason is saturation of the solution, or that some of the solids are irreversibly precipitated.

In step 114, standardization of the concentrated slurry takes place. The aim is to stabilize the extract by adding sufficient stabilizer (e.g. ascorbic acid and silica), and then titrating with a carrier such as maltodextrin to result in a final, known concentration of psychoactive alkaloids. The slurry is analyzed for dry mass concentration and alkaloid content. The liquid component of the concentrated slurry is first analyzed using a loss-on-drying analysis and high performance liquid chromatography coupled with diode array detection or mass spectrometry to determine the alkaloid content. Depending on the determined alkaloid content, non-toxic carriers are added to the concentrated slurry so as to provide a desired ratio between the weight of alkaloid and weight of carrier in the concentrated slurry. The added carriers, blending agents, excipients, flow aids etc. that may be used include maltodextrin from corn, potato or tapioca for example, gum arabic, silicon dioxide, microcrystalline cellulose, ascorbic acid, sodium benzoate, sodium phosphate, sodium citrate, rice hulls, and rice. A combination of any of these carriers may be used.

In step 116, the concentrated slurry is dried to remove the remaining solvent or water, resulting in a powdered psilocybin mushroom extract with a known concentration by weight of psychoactive compound(s). The extract is a powdered psilocybin mushroom extract that may have, for example, a total psychoactive alkaloid concentration of 0.1-10% by dry weight. Other compounds may be included in the extract. These may be sugars, proteins, carbohydrates and fats, and may make up about half of the extract. Step 116 is optional, as it may be the intention to produce a liquid extract instead of a powdered extract.

C. Exemplary Embodiments

75% Ethanol Solvent

Figure 2:
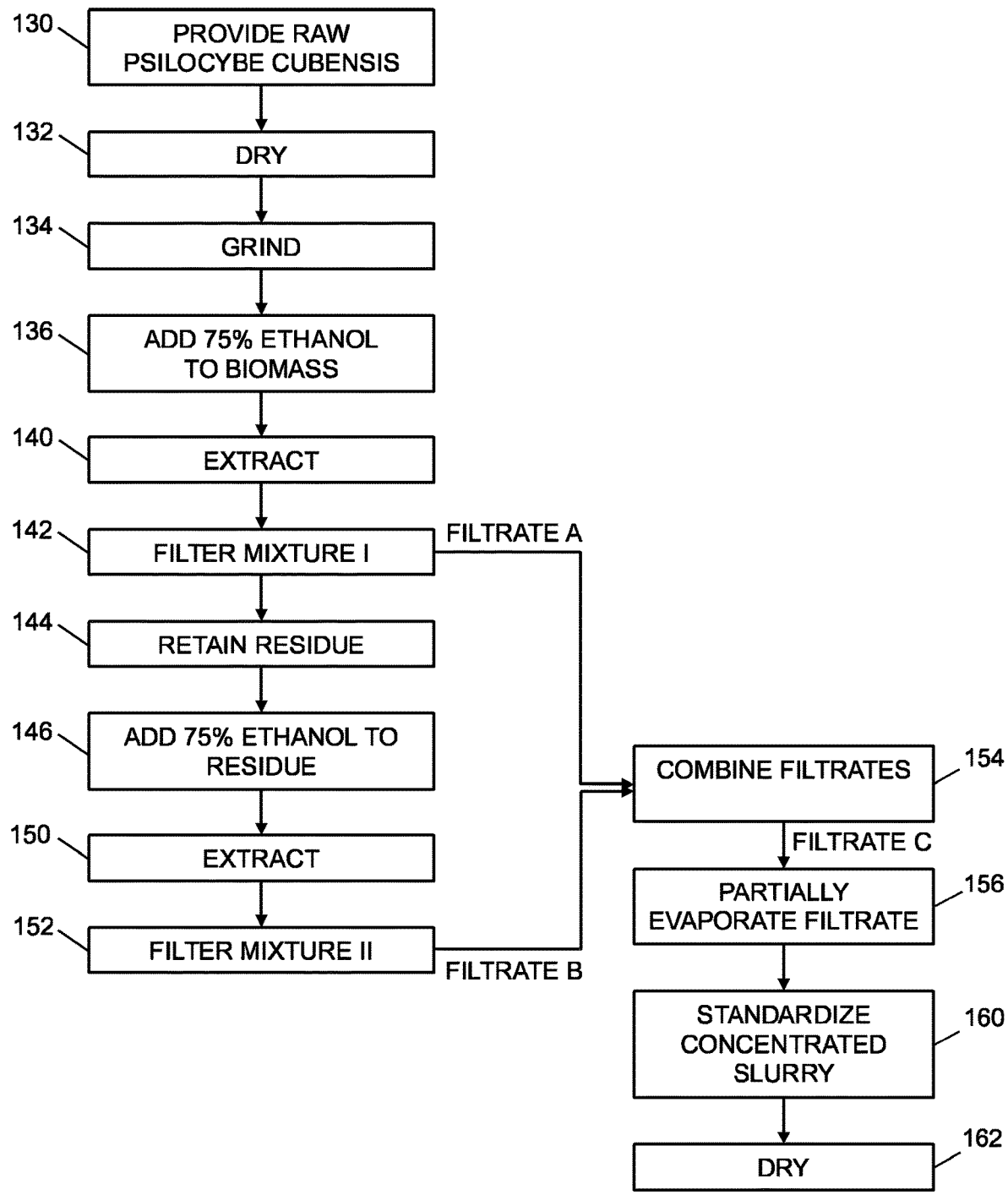
FIG. 2 is a flowchart showing more detailed steps of a process for extracting psychoactive alkaloids from *Psilocybe cubensis* using a 75% ethanol solvent, according to an embodiment of the present invention.

Referring to FIG. 2, an exemplary detailed process is shown for the extraction of psychoactive compounds from *Psilocybe cubensis* mushrooms using a 75% ethanol solvent In step 130, 2.5 kg of raw psilocybin mushrooms from the *Psilocybe cubensis* species is provided. In step 132, the raw psilocybin mushrooms are dried in a forced air oven at 25° C., for 10 hours. The aim is to dry the mushrooms so as not to significantly reduce their psychoactive alkaloid concentration. For example, if too high a temperature or too long a time at a specific temperature were used, the alkaloids may start to decompose. The resulting, dried biomass is 140 g. In step 134, the dried biomass is ground using a hammer mill or the equivalent, to a particle size of 200 mesh.

In step 136, a 5 kg quantity of the 75% (by weight) ethanol solvent, formed by mixing 3 parts of ethanol to 1 part of water by weight, is placed in an extraction vessel. The dried, ground biomass is also placed in the extraction vessel, which is heat-controlled and agitated.

The extraction proceeds in step 140 as the biomass soaks in the solvent. The temperature of the extraction process is 70° C., and the duration of extraction is 4 hours. The temperature remains constant during the extraction process.

In step 142, the resulting mixture of biomass solids and solvent with dissolved extract, is filtered while still hot, i.e. still at 70° C., or slightly lower due to ambient cooling. This removes a residue with undissolved psilocybin mushroom components from the filtrate. The filter used is a 10 pm sieve. The filtrate from this step is filtrate A. In step 144, the residue is retained and placed back into the extraction vessel. In step 146, another 5 kg of 75% ethanol is added to the retained residue.

In step 150, the extraction process of the residue continues at the same temperature as for the initial extraction step, i.e. at 70° C., for a time of 4 hours. Again, the temperature remains constant during the extraction process.

In step 152, the second resulting mixture, of biomass solids and solvent with dissolved extract, is filtered to remove the residue of unwanted solid material. The filter used is a 10 pm sieve. Note that in other embodiments a differently sized filter may be used here or in the prior filtration step, or the liquid may be decanted from the residue without filtering. In some embodiments, a centrifuge may be used to help separate the liquid from the residue. Filtrate B from the second filtration process may have a lower concentration of psychoactive compounds than filtrate A from the first filtration step. Filtrates A and B are then mixed in step 154 to result in bulk filtrate C. More extract can be obtained by splitting the solvent into two or more batches and using each one sequentially to soak the biomass, compared to using a single volume of solvent.

The bulk filtrate C is then processed with a rotary evaporator in step 156 to remove solvent until the volume of filtrate C is 2.5 liters. At this point, the reduced amount of filtrate C is a concentrated slurry, due to the precipitation of water-insoluble components, for example.

The volume of 2.5 L is chosen because the mixture now has a low enough ethanol content that the carriers can be mixed in. By preferentially removing ethanol over water, which occurs naturally during the evaporation, it also gives the later spray-drying step a lower risk of explosion compared to if a 75% ethanol slurry were sprayed directly.

In step 160, after some of the solvent has been removed using the rotary evaporator, the concentrated slurry is then standardized. The standardization process uses a titration procedure to determine the concentration of the psychoactive alkaloids in the concentrated slurry. The standardization procedure entails adjusting the concentration of psychoactive alkaloids the concentrated slurry to a desired target, such as 1.00% by dry weight. In this example, 4.7 g of ascorbic acid, 1.9 g of $SiO_2$ and 47 g of maltodextrin are added to the concentrated slurry.

In step 162, after the standardization process, the standardized concentrated slurry is dried using a bench-top spray dryer. This results in 100 g of powdered psilocybin mushroom extract with a total alkaloid concentration of 1.00% by weight. As can be seen, the purity of the extract can be defined as a percentage to a precision of two decimal places.

0-100% Ethanol Solvent

Figure 3:
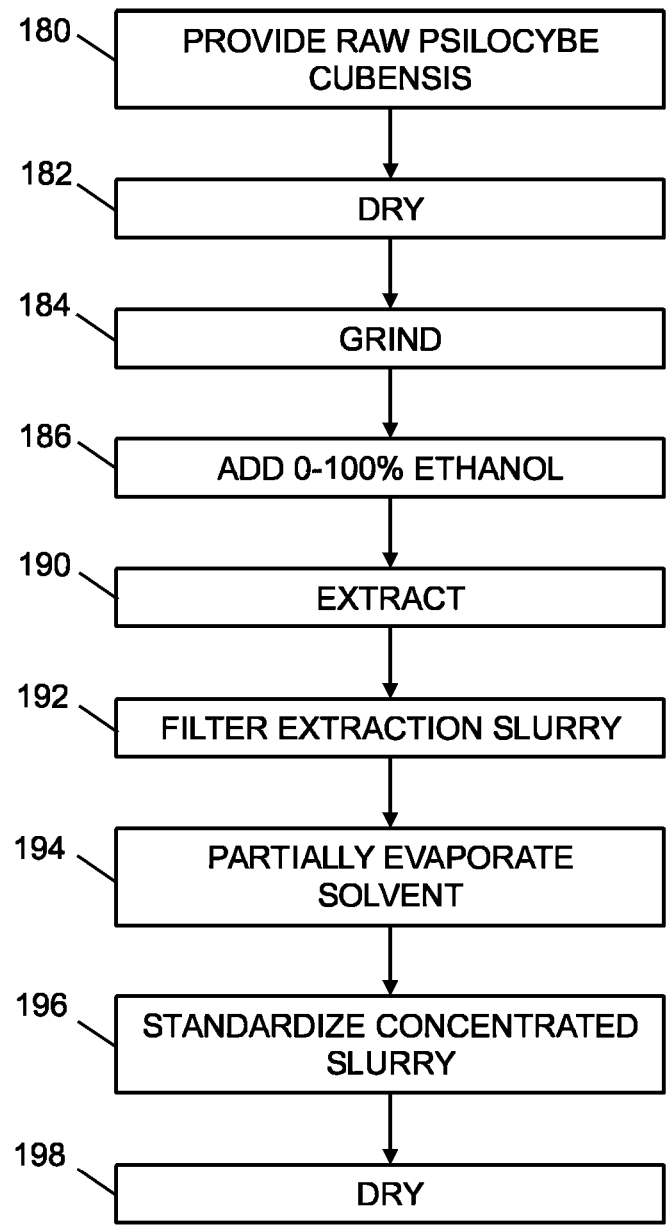
FIG. 3 is a flowchart showing more detailed steps of a process for extracting psychoactive alkaloids from *Psilocybe cubensis* using a hydro-ethanol solvent, according to an embodiment of the present invention.

Referring to FIG. 3, a process is shown for the extraction of psychoactive compounds from *Psilocybe cubensis* using a general hydro-ethanol solvent. The solvent may range from a percentage of <1% of ethanol in water to 100% ethanol.

In step 180, 2.5 kg of raw psilocybin mushrooms from the *Psilocybe cubensis* species is provided. In step 182, the raw *Psilocybe cubensis* is dried in a forced air oven at 25° C. for 10 hours. In step 184, the resulting dried biomass is ground in a hammer mill or the equivalent, to particle size of 200 mesh.

In step 186, 5 kg of solvent, having a 0-100% ethanol concentration is added to an extraction vessel into which the ground biomass is placed. The extraction vessel is an agitated, heat-controlled vessel.

In step 190, the extraction proceeds as the biomass is soaked. The temperature of the extraction is elevated above room temperature to 70° C. Temperature and pressure, if applied, are generally selected so that the solvent does not boil if elevated temperatures are used. The duration of the extraction is 4 hours.

In the step 192, the extraction slurry is filtered to remove residue with undissolved *Psilocybe cubensis* from the filtrate. The residue may be treated with another extraction step if desired, and if so, the filtrate from the subsequent step is combined with the filtrate from the first filtration.

In step 194, solvent from the filtrate is partially evaporated using a rotary evaporator. The resulting concentrated slurry is then subjected to a standardization process in step 196. The standardized concentrated slurry is then dried using a bench-top spray dryer in step 198 to result in a powder with an accurately determined concentration by weight of psychoactive alkaloids.

100% Water Solvent

Figure 4:
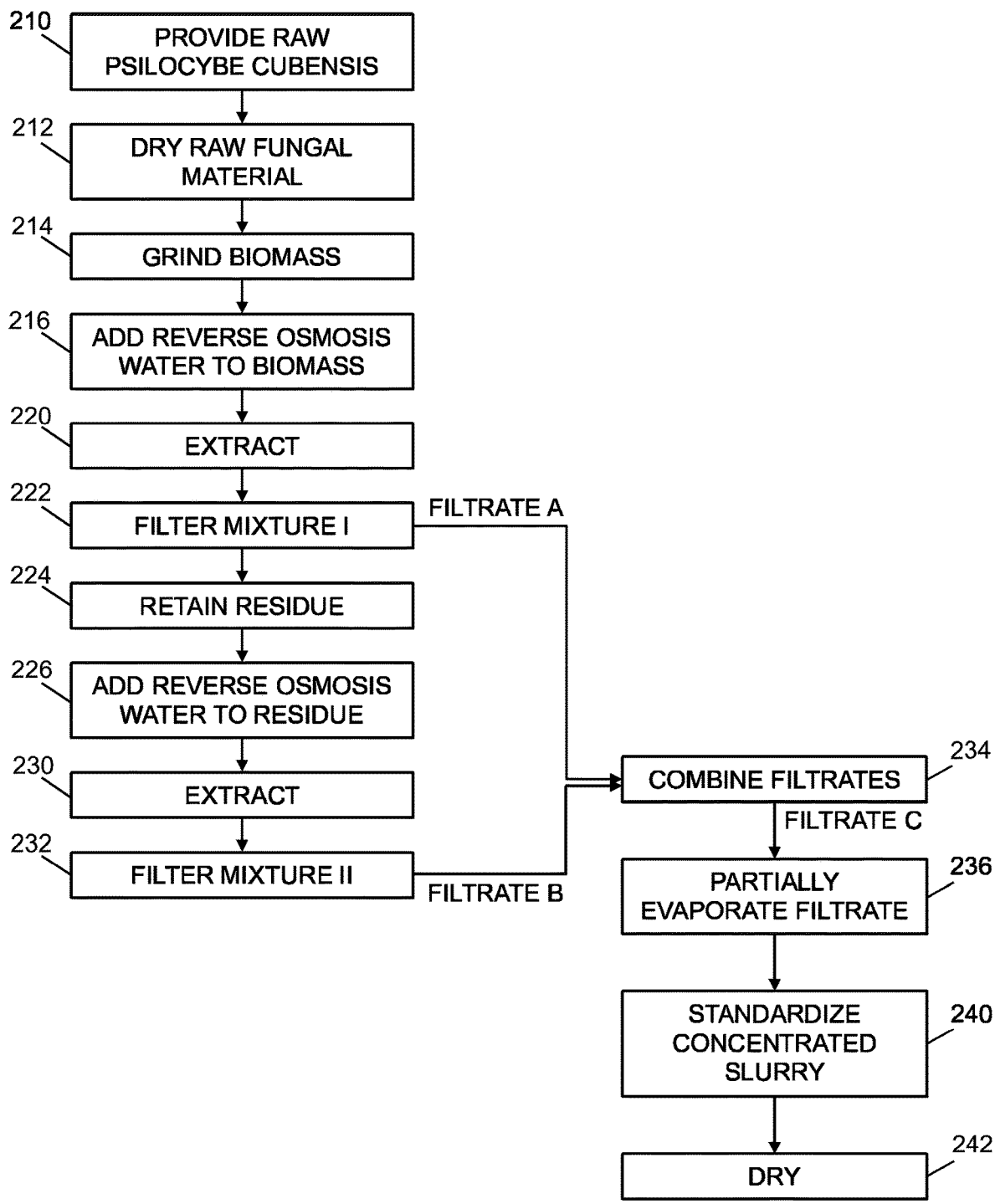
FIG. 4 is a flowchart showing more detailed steps of a process for extracting psychoactive alkaloids from *Psilocybe cubensis* using a water solvent, according to an embodiment of the present invention.

Referring to FIG. 4, a detailed process is shown for the extraction of psychoactive compounds *Psilocybe cubensis* using 100% reverse osmosis water as the solvent.

In step 210, 2.5 kg of raw psilocybin mushrooms from the *Psilocybe cubensis* species is provided. In step 212, the raw *Psilocybe cubensis* is dried in a forced air oven at 25° C. for 10 hours. The dried biomass is 140 g. Note that the dried biomass is the same weight in different examples because the mushrooms were from the same starting batch. In step 214, the dried biomass is ground in a hammer mill or the equivalent, to a particle size of 200 mesh.

In step 216, 5 liters of solvent, which is 100% reverse osmosis water, is placed in an extraction vessel with the dried biomass, which is heat-controlled and agitated.

In step 220, the extraction proceeds. The temperature of the extraction process is 90° C., and the duration of the extraction is 12 hours. In the step 222, the extraction slurry is filtered while still hot to remove residue with undissolved *Psilocybe cubensis* from the filtrate. The filtrate from this step is considered as filtrate A. In step 224, the residue is retained and placed back in the extraction vessel. In step 226, another 5 liters of 100% reverse osmosis water is added to the residue. In step 230, the extraction process of the residue continues at a temperature of 90° C., for 10 hours. The temperature remains constant during the extraction process. In step 232, the second resulting mixture, of biomass solids and water with dissolved extract, is filtered while still hot to remove the residue of unwanted solid material. Filtrates A and B are then mixed in step 234 to result in bulk filtrate C.

The bulk filtrate C is then processed with a rotary evaporator in step 236 to remove solvent until the volume of filtrate C is 2.5 liters. At this point, the reduced amount of filtrate C is a concentrated slurry, due to the precipitation of some of the psychoactive alkaloids.

In step 240, after some of the solvent has been removed using the rotary evaporator, the concentrated slurry is then standardized. The standardization process uses a titration procedure to determine the concentration of the psychoactive alkaloids in the concentrated slurry. The standardization procedure entails adjusting the concentration of the psychoactive alkaloids in the concentrated slurry to a desired dry target. In this example, 6.3 g of ascorbic acid, 2.5 g of $SiO_2$ and 63 g of maltodextrin are added to the concentrated slurry.

In step 242, after the standardization process, the standardized concentrated slurry is dried using a bench-top spray dryer. This results in 140 g of powdered psilocybin mushroom extract with a total alkaloid concentration of 0.50% by weight.

100% Methanol Solvent

Figure 5:
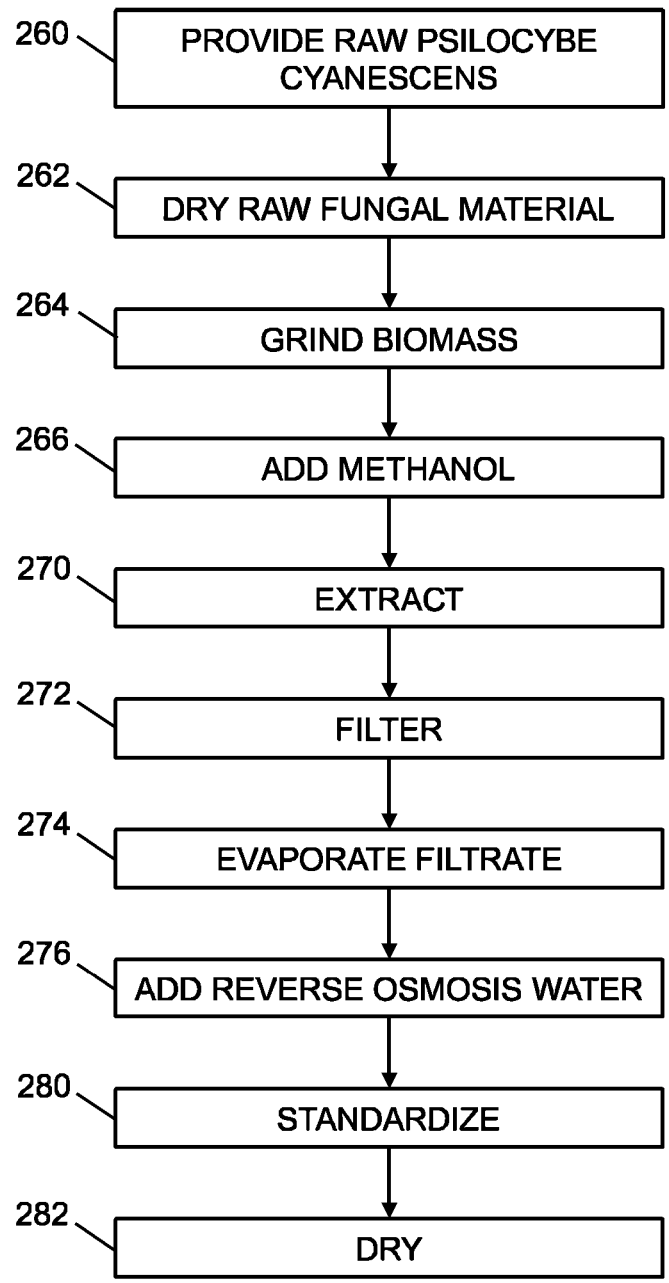
FIG. 5 is a flowchart showing more detailed steps of a process for extracting psychoactive alkaloids from *Psilocybe cyanescens* using a methanol solvent, according to an embodiment of the present invention.

Referring to FIG. 5, a process is shown for the extraction of psychoactive compounds from *Psilocybe cyanescens* mushrooms using 100% methanol as the solvent.

In step 260, 2.5 kg of raw psilocybin mushrooms from the *Psilocybe cyanescens* species is provided. In step 262, the raw *Psilocybe cyanescens* is dried in a forced air oven at 25° C. for 10 hours. The dried biomass is 140 g. In step 264, the dried biomass is ground in a cutting mill or the equivalent, to particle size of 200 mesh. In step 266, 5 kg of solvent, which is 100% methanol, is added to an extraction vessel, which is heat-controlled and agitated. The dries biomass is also added to the extraction vessel.

In step 270, the extraction proceeds. The temperature of the extraction process is a constant 25° C., and the duration of the extraction is 4 hours. A pressure of 100 kPa above atmospheric (15 psig) is applied to the mixture of solvent and biomass during the extraction. In step 272, the extraction slurry is filtered to remove residue with undissolved *Psilocybe cyanescens* from the filtrate.

The filtrate is then processed with a rotary evaporator in step 274 to evaporate all the methanol from the filtrate. In this embodiment, all the solvent is removed at this stage because methanol is not regarded as safe for human consumption, and there should be no trace amounts of it remaining in the final product. In step 276, 1.25 liters of reverse osmosis water at room temperature is added to the solid that is remaining after the evaporation step, to form a concentrated slurry.

In step 280, the concentrated slurry is standardized. In this example, 1.84 g of $SiO_2$ and 46 g of maltodextrin are added to the concentrated slurry. In step 282, the standardized concentrated slurry is dried using a bench-top spray dryer. This results in 95 g of powdered psilocybin mushroom extract with a total alkaloid concentration of 1.50% by weight.

Acidic Solvent

Figure 6:
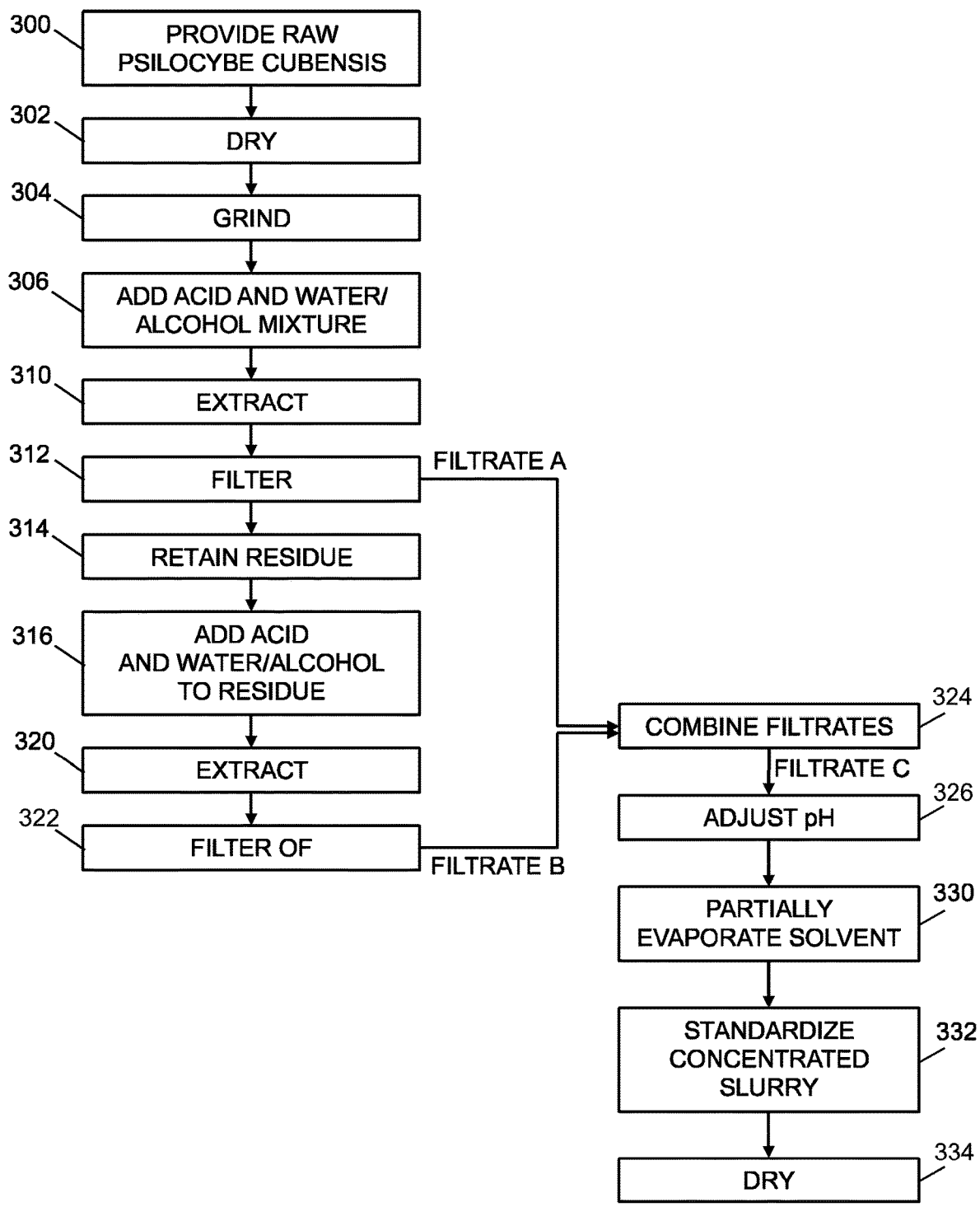
FIG. 6 is a flowchart showing more detailed steps of a process for extracting psychoactive alkaloids from *Psilocybe cubensis* using a buffered acidic solvent, according to an embodiment of the present invention.

Referring to FIG. 6, a process is shown for the extraction of psychoactive compounds from *Psilocybe cubensis* mushrooms using a buffered acidic solvent. In step 300, 2.5 kg of raw psilocybin mushrooms from the *Psilocybe cubensis* species is provided. In step 302, the raw *Psilocybe cubensis* is dried in a forced air oven at 25° C. for 5-10 hours. The dried biomass is 140 g. In step 304, the dried biomass is ground in a hammer mill or the equivalent, to particle size of 200 mesh.

In step 306, 5 L of solvent is added with the dried biomass to an extraction vessel, which is heat-controlled and agitated. The solvent is a pH-adjusted, hydro-ethanol mixture.

For its preparation, 44 g of anhydrous citric acid is placed into a 5 L vessel with 1.25 L of reverse osmosis water followed by 3.75 L of ethanol. The contents are mixed until completely dissolved. The pH of this solution is between pH 1.8 and pH 3.

In step 310, the extraction proceeds. The temperature of the extraction process is 30° C., and the duration of the extraction is 4 hours. In step 312, the extraction slurry is filtered to remove residue with undissolved *Psilocybe cubensis* from the filtrate. The filtrate from this step is named filtrate A. In step 314, the residue is retained and placed back in the extraction vessel. In step 316, another 5 L of the same solvent is added to the residue. In step 320, the extraction process of the residue continues at a temperature of 30° C., for 4 hours. The temperature remains constant during the extraction process. In step 322, the second extraction slurry is filtered, to remove the residue of unwanted solid material. Filtrates A and B are then mixed in step 324 to result in bulk filtrate C.

Bulk filtrate C is then brought to a pH of 5 with 5M sodium hydroxide. The amount of the sodium hydroxide depends on the specific mushroom matrix extracted, and is not possible to predict accurately. The pH-adjusted, concentrated slurry is then processed with a rotary evaporator in step 330 to remove solvent until the volume of filtrate C is 2.5 liters. At this point, the reduced amount of filtrate C is a concentrated slurry, due to the precipitation of some of the psychoactive alkaloids.

In step 332, the concentrated slurry is then standardized. In this example, 4.7 g of ascorbic acid, 1.9 g of $SiO_2$ and 47 g of maltodextrin are added to the concentrated slurry. In step 334, the standardized concentrated slurry is dried using a bench-top spray dryer. This results in 100 g of powdered psilocybin mushroom extract with a total alkaloid concentration of 1.00% by weight.

Alkaline Solvent

Figure 7:
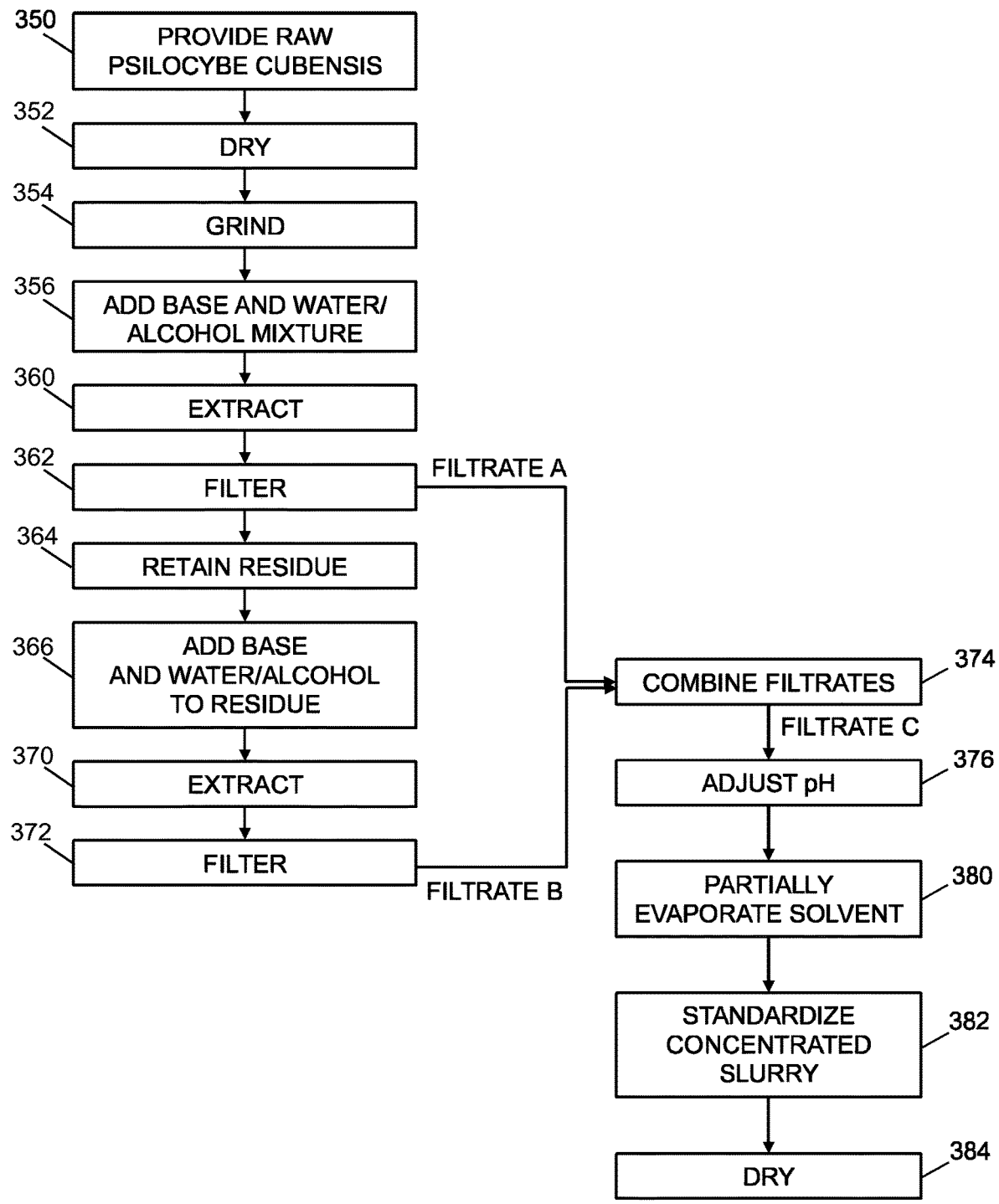
FIG. 7 is a flowchart showing more detailed steps of a process for extracting psychoactive alkaloids *Psilocybe cubensis* using a buffered alkaline solvent, according to an embodiment of the present invention.

Referring to FIG. 7, a process is shown for the extraction of psychoactive compounds from *Psilocybe cubensis* mushrooms using a buffered alkaline solvent. In step 350, 2.5 kg of raw psilocybin mushrooms from the *Psilocybe cubensis* species is provided. In step 352, the raw *Psilocybe cubensis* is dried in a forced air oven at 25° C. for 10 hours. The dried biomass is 140 g. In step 354, the dried biomass is ground in a hammer mill or the equivalent, to a particle size of 200 mesh.

In step 356, 5 liters of solvent is added with the biomass to an extraction vessel, which is heat-controlled and agitated. The solvent is a pH-adjusted, hydro-ethanol mixture. For its preparation, 200 g of sodium hydroxide pellets are placed into a 5 L vessel, with 1.25 L of reverse osmosis water followed by 3.75 L of ethanol. The contents are mixed until completely dissolved. The pH of this solution is between pH 11 and pH 12.

In step 360, the extraction proceeds. The temperature of the extraction process is 30° C., and the duration of the extraction is 4 hours. In step 362, the extraction slurry is filtered to remove residue with undissolved *Psilocybe cubensis* from the filtrate. The filtrate from this step is named filtrate A. In step 364, the residue is retained and placed back in the extraction vessel. In step 366, another 5 L of the same solvent is added to the residue. In step 370, the extraction process of the residue continues at a temperature of 30° C., for 4 hours. The temperature remains constant during the extraction process. In step 372, the second extraction slurry is filtered, to remove the residue of unwanted solid material. Filtrates A and B are then mixed in step 374 to result in bulk filtrate C.

Bulk filtrate C is then brought to a pH of 5 with sufficient 5M phosphoric acid. The pH-adjusted concentrated slurry is then processed with a rotary evaporator in step 380 to remove solvent until the volume of filtrate C is 2.5 liters. At this point, the reduced amount of filtrate C is a concentrated slurry, due to the precipitation of some of the psychoactive alkaloids.

In step 382, the concentrated slurry is then standardized. In this example, 4.7 g of ascorbic acid, 1.9 g of $SiO_2$ and 47 g of maltodextrin are added to the concentrated slurry. In step 384, the standardized concentrated slurry is dried using a bench-top spray dryer. This results in 100 g of powdered psilocybin mushroom extract with a total alkaloid concentration of 1.00% by weight.

D. Apparatus

Figure 8:
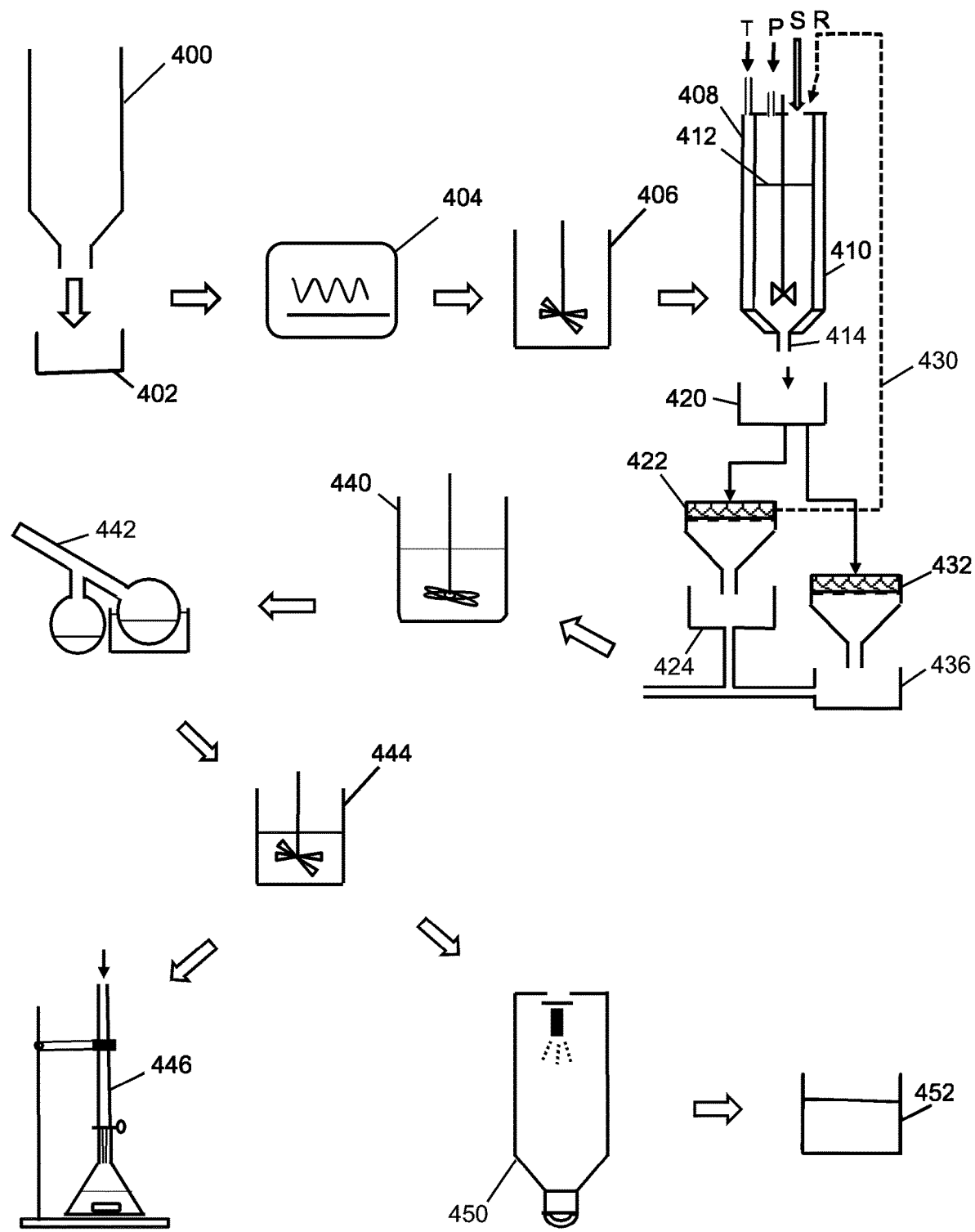
FIG. 8 is a schematic diagram of the apparatus used for the extraction of psychoactive compounds according to an embodiment of the present invention.

Referring to FIG. 8, an example of the apparatus is shown schematically. Raw psilocybin mushrooms are provided in a hopper 400, for example, and are released in batches into container 402. The raw fungal material is then dried in a forced air oven 404. The dried biomass is placed into a grinder 406 for grinding.

After the drying and grinding steps, the ground biomass is placed in an agitated, heat-controlled extraction vessel 410. The vessel holds the biomass and solvent 412, such as lower aliphatic alcohols, water, buffered acid or buffered alkaline, or a mixture thereof. The vessel may be surrounded by an insulating wall 408. Alternately, there may be an insulating jacket wrapped around the vessel. The insulating wall 408 or jacket helps to maintain the contents 412 under a constant temperature (T) between 5-95° C. The pressure (P) inside the extraction vessel 410 may be regulated up to 100 MPa (15000 psig).

After the extraction, the bottom of the extraction vessel 410 is opened at outlet 414 and the extraction slurry is collected in container 420. The extraction slurry is then fed into filter 422. After filtration, the first filtrate leaves the filter 422 and is collected in container 424. The residue 430 is then fed back at R into agitated, heat-controlled vessel 410 and more solvent (S) is added. After the second extraction, the extraction slurry is collected in container 420 and is then fed into filter 432 (or filter 422). After filtration, the second filtrate and solvent mixture leaves the filter 432 and is collected in container 436.

After the two filtration stages, if there are two, the filtrates are mixed in container 440. Otherwise, if there is only a single filtration step, mixing is unnecessary. Neutralizer is added as necessary to the filtrate in container 440. The extraction slurry, pH-adjusted where necessary, is then passed to rotary evaporator 442 in which all or part of the solvent is evaporated, depending on the embodiment. If all the solvent is evaporated, then reverse osmosis water is added to the solids remaining after the evaporation.

The concentrated slurry is then passed to container 444 and tested to determine its alkaloid content, using a titration setup 446. Carriers are added to container 444 with the concentrated slurry, and mixed. The standardized slurry is then placed in a bench-top spray drier 450 to produce psilocybin mushroom extract that is collected in container 452.

E. Variations

Other embodiments are also possible. While only specific neutralizing agents, food grade acids and food grade bases have been mentioned herein, other neutralizing agents, food grade acids and food grade bases may be used.

In general, unless otherwise indicated, singular elements may be in the plural and vice versa with no loss of generality.

Temperatures that have been given to the nearest degree include all temperatures within a range of ±0.5° C. of the given value. Likewise, numbers and percentages are specified to the nearest significant digit. Values of pH are specified to ±0.5

While exemplary pH ranges are given in some examples, other pH ranges are possible.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Steps in the flowchart may be performed in a different order, other steps may be added, or one or more may be removed without altering the main outcome of the process.

In other embodiments, other drying techniques, temperatures and durations may be used. It is possible in other embodiments to grind the dried biomass to lower or higher particle size than 200 mesh. For example, grinding to a mesh size of 40 would work in some embodiments. The choice of solvent may have an impact on which mesh size to grind the dried mushrooms to. Note that, in other embodiments, the grinding step 334 may take place before or after the drying step 332.

Water purified by other purification technologies may be used instead of reverse osmosis water. In alternative embodiments the solvent is 0.02% to 1.5% acetic acid in water. In alternate embodiment, the solvent comprises 75% ethanol, 25% water and 0.1M sodium hydroxide. In alternative embodiments the solvent is a hydro-methanol mixture, with a methanol content in the range of below 1% to 100%. The solvent may also be propan-1-ol, propan-2-ol, a butanol isomer, or a mixture of any or all of these with water, in any percentage ratio.

Any of the solvents described herein may be used with any of the mushroom varieties that include psychoactive alkaloids.

The process may be scaled up using larger quantities and modified apparatus.

The extraction process in other embodiments may use varying applied pressures and temperatures, which vary during the soaking steps.

All parameters, dimensions, materials, quantities and configurations described herein are examples only and may be changed depending on the specific embodiment. Accordingly, the scope of the invention is to be construed in accordance with the substance defined by the following claims.

The invention claimed is:

1. A process for forming an extract with a specified concentration of psychoactive alkaloids from a dried, raw, psilocybin fungus comprising the steps of:
   soaking a biomass of the dried, raw psilocybin fungus in a solvent that is water or aqueous acid in order to dissolve the psychoactive alkaloids in the solvent, wherein a pressure of 50 kPa 100 MPa is applied during the soaking;
   filtering an undissolved portion of the biomass from the solvent;
   evaporating a portion of the solvent to form a concentrated slurry;
   measuring a psychoactive alkaloid content in the concentrated slurry;
   measuring a dry mass content in the concentrated slurry;
   using the psychoactive alkaloid content, the dry mass content and the specified concentration to determine a quantity of a carrier to add to the concentrated slurry in order to obtain the specified concentration of the psychoactive alkaloids in the extract;
   standardizing the concentrated slurry by adding the quantity of the carrier to the concentrated slurry; and
   drying the concentrated slurry to result in the extract with the specified concentration of the psychoactive alkaloids.

2. The process of claim 1, wherein the extract is a powdered extract.

3. The process of claim 1, wherein the solvent is purified water.

4. The process of claim 1, wherein the solvent is reverse osmosis water.

5. The process of claim 1, wherein the aqueous acid is a buffered acid.

6. The process of claim 1, wherein the aqueous acid is a strong acid buffer.

7. The process of claim 1, wherein the aqueous acid is 0.02-1.5% acetic acid.

8. The process of claim 1, wherein the solvent is aqueous acid, and the process further comprises, between the filtering and evaporating steps, adjusting the solvent to a pH of 4-9.

9. The process of claim 1, wherein the soaking step is at a temperature of 5-95° C.

10. The process of claim 1, wherein the soaking step is at a temperature of 90° C.

11. The process of claim 10, wherein the filtering step occurs while the solvent is still hot.

12. The process of claim 1, comprising agitating the solvent during the soaking step, wherein the soaking step has a duration of 10 minutes to 12 hours.

13. The process of claim 1, wherein the soaking step has a duration of 12 hours.

14. The process of claim 1, wherein the psilocybin fungus is *Psilocybe cubensis, Psilocybe cyanescens*, or both *Psilocybe cubensis* and *Psilocybe cyanescens*.

15. The process of claim 1, wherein the psychoactive alkaloids comprise psilocybin, psilocin, baeocystin, norbaeocystin, or any mixture thereof.

16. The process of claim 1, wherein a solvent to biomass ratio is in a range from 1L:1kg to 50L:1kg.

17. The process of claim 1, wherein the specified concentration is 0.1-10% by weight.

18. The process of claim 1, wherein the specified concentration is specified as a percentage with a precision of two decimal places.

19. The process of claim 1, wherein the carrier comprises ascorbic acid, silicon dioxide, maltodextrin, gum arabic, microcrystalline cellulose, sodium citrate, sodium benzoate, sodium phosphate, rice, rice hulls, or any combination selected therefrom.

20. The process of claim 1, further comprising:
   repeating, using further solvent, the soaking and filtering steps for the undissolved portion of the biomass; and combining the solvent, after filtering the solvent, with the further solvent, after filtering the further solvent.

21. The process of claim 1, wherein the dried, raw, psilocybin fungus is ground to a mesh size of 40-200.

* * * * *